(12) United States Patent
Beltman et al.

(10) Patent No.: US 11,684,516 B2
(45) Date of Patent: Jun. 27, 2023

(54) HEARING PROTECTION AND COMMUNICATION APPARATUS USING VIBRATION SENSORS

(71) Applicant: Intel Corporation, Santa Clara, CA (US)

(72) Inventors: Willem M. Beltman, West Linn, OR (US); Hector A. Cordourier Maruri, Guadalajara (MX); Paulo Lopez Meyer, Tlaquepaque (MX); Jonathan Huang, Pleasanton, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 17/322,380

(22) Filed: May 17, 2021

(65) Prior Publication Data

US 2021/0267803 A1    Sep. 2, 2021

Related U.S. Application Data

(63) Continuation of application No. 15/912,006, filed on Mar. 5, 2018, now Pat. No. 11,007,081.

(51) Int. Cl.
| | | |
|---|---|---|
| *A61F 9/02* | (2006.01) | |
| *G10L 15/20* | (2006.01) | |
| *A61F 11/06* | (2006.01) | |
| *A61F 11/08* | (2006.01) | |

(Continued)

(52) U.S. Cl.
CPC .............. *A61F 9/029* (2013.01); *A61F 11/06* (2013.01); *G10L 15/20* (2013.01); *A61F 11/08* (2013.01); *A61F 11/145* (2022.01); *G02C 11/06* (2013.01)

(58) Field of Classification Search
CPC .......... A61F 9/029; A61F 11/06; A61F 11/08; A61F 11/145; G10L 15/20; G10L 15/16; G10L 25/51; G10L 25/78; G10L 21/0208; G02C 11/06; H04R 1/46; H04R 2460/13; A61B 5/6803; A61B 5/4504; A61B 5/721; G10K 11/17823
See application file for complete search history.

(56) References Cited

U.S. PATENT DOCUMENTS

| | | |
|---|---|---|
| 8,157,730 B2 | 4/2012 | LeBoeuf et al. |
| 10,631,113 B2 | 4/2020 | Mishra et al. |
| 11,007,081 B2 | 5/2021 | Beltman et al. |

(Continued)

OTHER PUBLICATIONS

The National Academies of Sciences Engineering Medicine, "Technology for a Quieter America," The National Academies Press, 2010, available at http://nap.edu/12928, 211 pages.

(Continued)

*Primary Examiner* — Yogeshkumar Patel
(74) *Attorney, Agent, or Firm* — Hanley, Flight & Zimmerman, LLC

(57) ABSTRACT

Hearing protection and communication apparatus using vibration sensors are disclosed. An example wearable electronic device includes means for transducing vibrations associated with speech into a first signal; means for transducing sound associated with ambient noise into a second signal; and means for processing to cause a speaker to output a signal to reduce the ambient noise; detect an identifier in the speech; and cause audio data representative of the speech to be transmitted to a second device associated with the identifier.

20 Claims, 9 Drawing Sheets

(51) Int. Cl.
  *G02C 11/06* (2006.01)
  *A61F 11/14* (2006.01)

(56) References Cited

U.S. PATENT DOCUMENTS

| | | |
|---|---|---|
| 2005/0141730 A1 | 6/2005 | Murphy |
| 2008/0008344 A1 | 1/2008 | Wakabayashi et al. |
| 2012/0282976 A1* | 11/2012 | Suhami ............ G10K 11/17857 |
| | | 381/314 |
| 2015/0319546 A1* | 11/2015 | Sprague ............... H04R 1/1066 |
| | | 381/312 |
| 2015/0326965 A1 | 11/2015 | Sprague et al. |
| 2016/0217367 A1* | 7/2016 | Moreno ................. G06N 3/045 |
| 2018/0301011 A1 | 10/2018 | Werner et al. |
| 2019/0045298 A1* | 2/2019 | Klemme ............. G10L 21/0208 |
| 2021/0267803 A1 | 9/2021 | Beltman et al. |

OTHER PUBLICATIONS

United States Patent and Trademark Office, "Non-Final Office Action," issued in connection with U.S. Appl. No. 15/912,006, dated Sep. 22, 2020, 19 pages.

United States Patent and Trademark Office, "Notice of Allowance and Fee(s) Due," issued in connection with U.S. Appl. No. 15/912,006, dated Jan. 15, 2021, 9 pages.

* cited by examiner

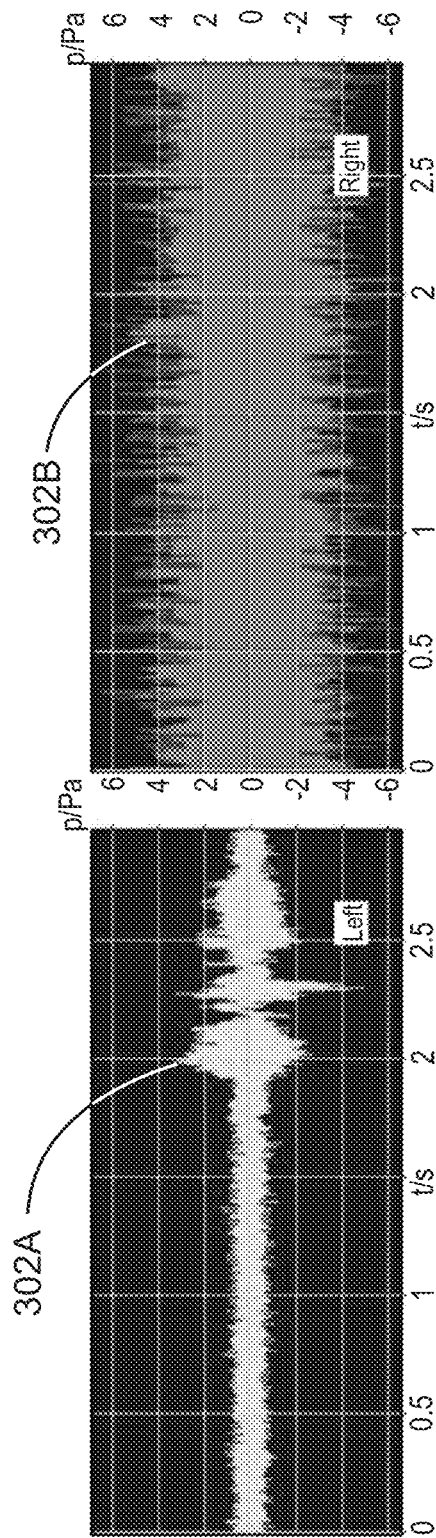
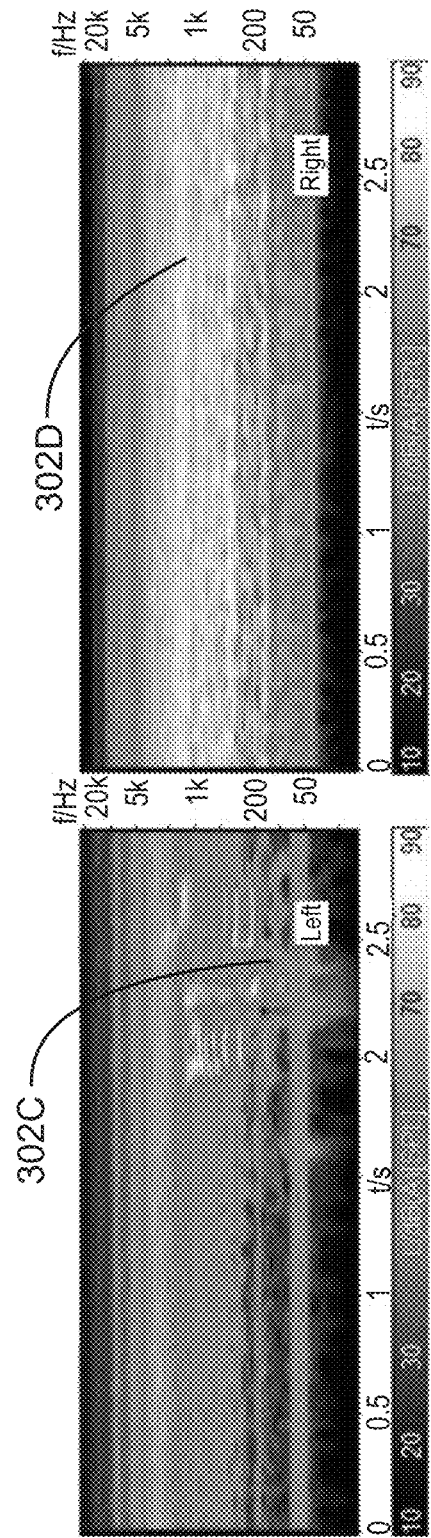
FIG. 3A  FIG. 3B  FIG. 3C  FIG. 3D

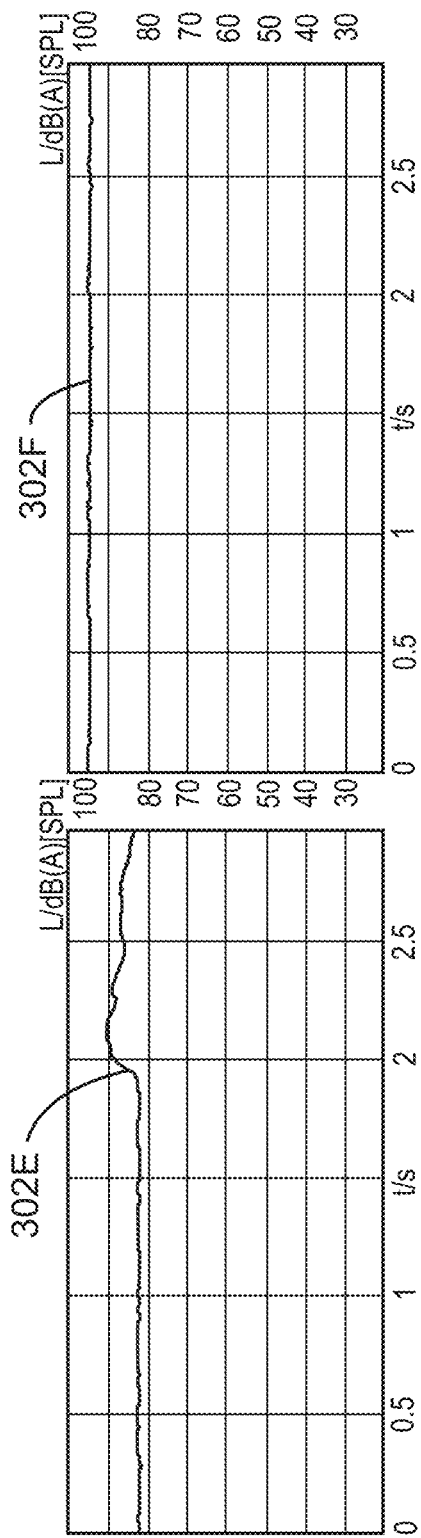

US 11,684,516 B2

HEARING PROTECTION AND COMMUNICATION APPARATUS USING VIBRATION SENSORS

RELATED APPLICATION

This patent arises from a continuation of U.S. patent application Ser. No. 15/912,006, now U.S. Pat. No. 11,007,081, which was filed on Mar. 5, 2018. U.S. patent application Ser. No. 15/912,006 is hereby incorporated herein by reference in its entirety. Priority to U.S. patent application Ser. No. 15/912,006 is hereby claimed.

BACKGROUND

Hearing protection devices may be used to protect ears from damage to the tympanic membrane or the nerves of the cochlea in the ears. For example, such hearing protection devices may include ear muffs, ear plugs, or headphones with noise cancellation technology.

BRIEF DESCRIPTION OF THE DRAWINGS

FIG. 3A is a diagram illustrating an example graph of a raw signal including speech captured from a vibration sensor;

FIG. 3B is a diagram illustrating an example graph of a raw signal including speech captured from a microphone in a noisy environment;

FIG. 3C is a diagram illustrating an example graph of a processed signal including speech captured from a vibration sensor in a noisy environment;

FIG. 3D is a diagram illustrating an example graph of a processed signal including speech captured from a microphone in a noisy environment;

FIG. 3E is a diagram illustrating an example graph of another processed signal including speech captured from a vibration sensor in a noisy environment;

FIG. 3F is a diagram illustrating an example graph of another processed signal including speech captured from a microphone in noisy environment;

The same numbers are used throughout the disclosure and the figures to reference like components and features. Numbers in the 100 series refer to features originally found in FIG. 1; numbers in the 200 series refer to features originally found in FIG. 2; and so on.

DESCRIPTION OF THE EMBODIMENTS

As discussed above, hearing protection devices may be used to protect ears from injuries caused by exposure to environments with high levels of noise. For example, workers in high noise environments of 85 decibels or louder may wear ear muffs or ear plugs to prevent hearing loss associated with extended exposure to high levels of noise. In some examples, users may use passive or active hard shell protectors or foam type inserts in the ear canal. However, using hearing protectors may also prevent effective communication between users because all sounds are equally diminished by these devices. Moreover, some workers may not use the hearing protection devices in order to effectively communicate. For example, workers may take off the ear muffs or ear plugs in order to hear another worker yelling over a high level of noise.

The present disclosure relates generally to techniques for communication and hearing protection. Specifically, the techniques described herein include an apparatus, method and system for communication and hearing protection in high noise environments. An example apparatus includes safety glasses including a vibration sensor to capture speech from a user. The apparatus includes hearing protectors communicatively coupled to the safety glasses and one or more other devices. The hearing protectors are to reduce a volume of an ambient sound and play back captured speech from the one or more other devices.

The techniques described herein thus enable users to communicate clearly in high noise environments and also be aware of their surroundings. At the same time, the techniques described herein also provide effective hearing protection. Moreover, the techniques may provide increased awareness of an environment. For example, the techniques described herein may be used to generate notifications based on particular ambient sounds detected in an environment. In addition, the techniques described herein may allow automated communication with other devices using speech commands. For example, speech captured using vibration sensors may be automatically sent to one or more other devices based on one or more detected keywords in the speech.

Figure 1:
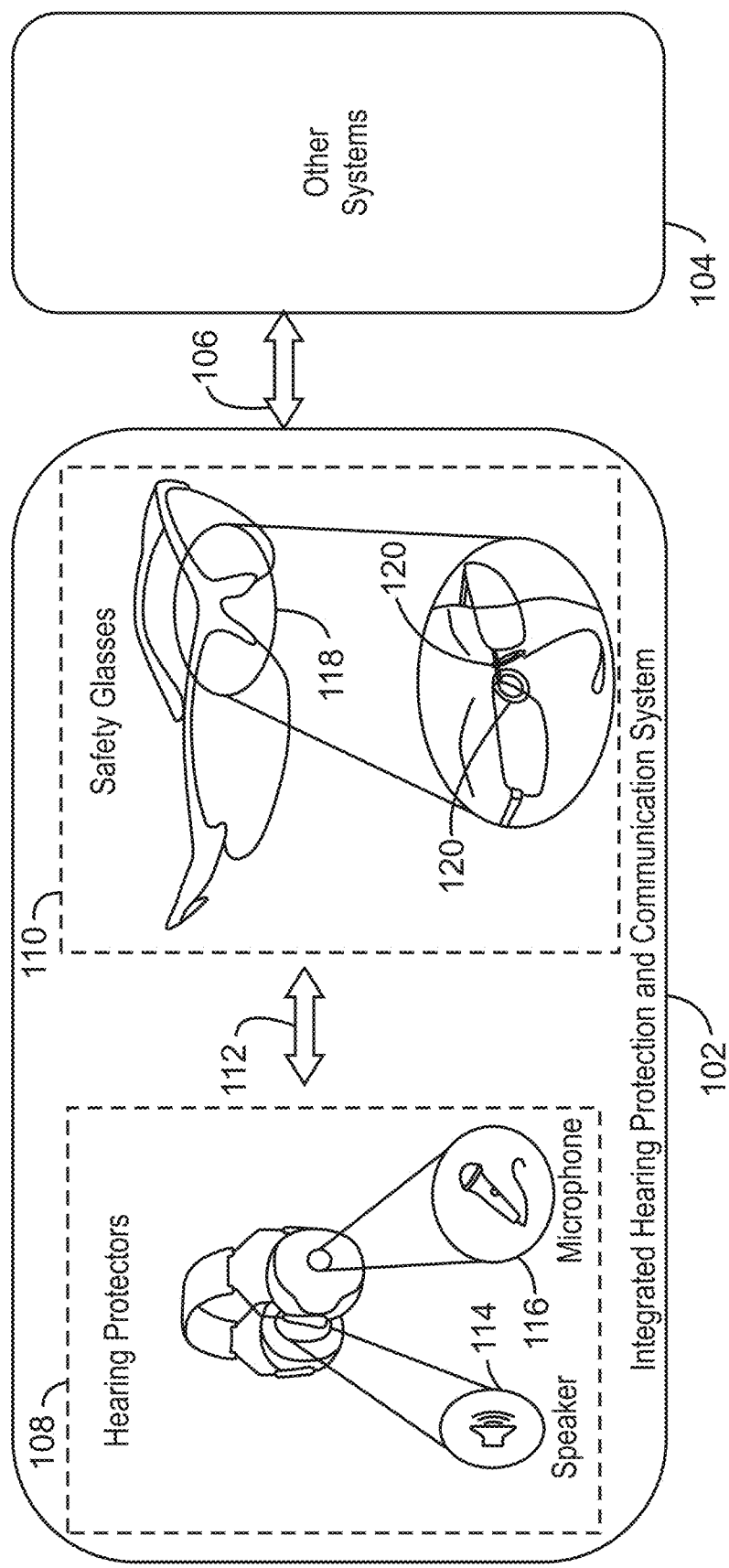
FIG. 1 is a block diagram illustrating an example system for communication and ear protection in noisy environments.

FIG. 1 is a block diagram illustrating an example system for communication and ear protection in noisy environments. The example system is referred to generally by the reference number 100 and can be implemented in the computing device 700 below in FIG. 7 using the process 200 or methods 400-600 of FIGS. 2 and 4-6 below.

The example system 100 includes an integrated hearing protection and communication system 102 communicatively coupled via a wireless connection 106 to one or more other systems 104. For example, the wireless connection 112 can be a short-range wireless connection such as a Bluetooth®, Wi-Fi®, or cellular connection. In some examples, the other systems may include other integrated hearing protection and communication systems, automated speech recognition (ASR) systems, and natural language processing (NLP) systems, among other external systems. The integrated hearing protection and communication system 102 includes hearing protectors 108 and safety glasses 110 communicatively coupled via a wireless connection 112. For example, the wireless connection 112 can be a short-range wireless connection such as a Bluetooth®, Wi-Fi® or cellular connection. The hearing protector 108 includes at least one speaker 114 and at least one microphone 116. The safety glasses 110 include a nose pad 118. The nose pad 118 includes vibration sensors 120. For example, the vibration sensors 120 can be piezoelectric elements or accelerometers.

As shown in FIG. 1, an integrated hearing and protection and communication system 102 can be used to protect ears from high noise environments while allowing communication with one or more other systems 104. For example, the hearing protector 108 can reduce the volume of ambient sounds in a high noise environment. The vibration sensors 120 of the safety glasses 110 can be used to capture speech of a user wearing the integrated hearing protection and communication system 102. For example, the vibration sensors 120 can capture vibrations of a user's nose when the user speaks. In some examples, the integrated hearing and protection and communication system 102 can be paired before use. For example, the hearing protector 108 can be paired with the safety glasses 110 via the wireless connection 112 before the use of the integrated hearing protection and communication system 102. In some examples, the integrated hearing protection and communication system 102 may also receive a unique identifier from the user. For example, the unique identifier may be in the form of a name or a personal identification number. In some examples, the integrated hearing protection and communication system 102 can then use the unique identifier for identification when connecting to other systems 104, such as nearby trusted devices or networks, via the wireless connection 116.

As shown in FIGS. 3A and 3C below, vibration sensors 120 can capture speech in noisy environments with reduced effects from ambient sounds. In some examples, the captured speech can be processed to remove nonlinear distortion based on a detected active voice call, as described in greater detail below. For example, speech that has an active voice call with a destination of a second integrated hearing protection and communication system 104 can be processed using a human-to-human voice transformation that enables another speaker to understand the speech in addition to being processed using an ASR voice transformation that improves the detectability of words and keywords in the speech. In some examples, speech that is captured without any detected active voice call can be processed using an ASR voice transformation that improves the detectability of words and keywords in the speech and be sent for processing at an ASR system 104. The processed speech can then be sent as input into an ASR engine. In some examples, the safety glasses 110 may include a speech interface. For example, the speech interface may include a local keyword recognition or an ASR module.

In some examples, the safety glasses 110 may be communicatively paired with a high quality hearing protectors. For example, the hearing protector 108 may include small speakers on the inside for playback of speech, ambient sounds, and notifications. In some examples, the hearing protector 108 may also include microphones 116 mounted on the outside of the protector to captured ambient sounds. In some examples, the hearing protector 108 may include on-board processing for audio event detection, loudness equalization, and sound logging for analysis of long term exposure to high volume environments, as described in detail with respect to FIG. 6 below.

The diagram of FIG. 1 is not intended to indicate that the example system 100 is to include all of the components shown in FIG. 1. Rather, the example system 100 can be implemented using fewer or additional components not illustrated in FIG. 1 (e.g., additional integrated hearing protection and communication systems, speakers, microphones, vibration sensors, safety glasses, hearing protectors, etc.).

Figure 2:
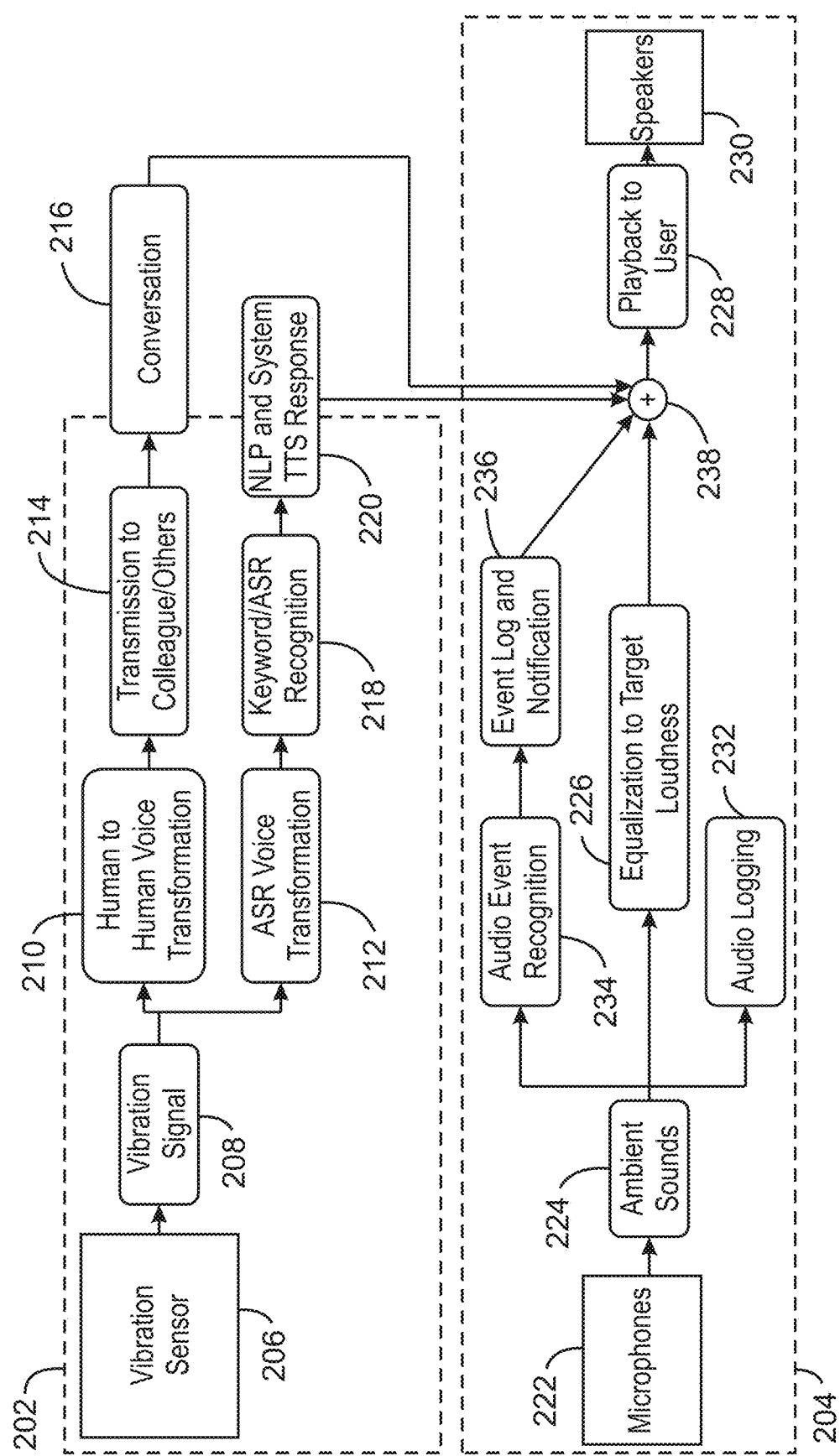
FIG. 2 is a flow chart illustrating an example process for communication and ear protection in noisy environments.

FIG. 2 is a flow chart illustrating an example process for communication and ear protection in noisy environments. The example process is generally referred to by the reference number 200 and can be implemented in the system 100 above or the computing device 700 below.

At block 202, a processor within a set of safety glasses captures speech via at least one vibration sensor, transforms the processed speech based on whether an active voice call is detected, and receives responses to the processed speech.

At block 204, a processor within a hearing protector captures ambient sounds from a microphone and processes the ambient sounds, along with speech from the safety glasses and other devices.

At block 206, a vibration sensor captures vibrations from around, near, or at a user's nose and generates a vibration signal 208. For example, the vibration signal 208 may include speech from a user. The vibration signal 208 may then be filtered for conversation or ASR voice transformation using on-board signal processing at blocks 210 and 212.

At block 210, a processor processes the vibration signal 208 with a human-to-human voice transformation such that the speech can be deciphered by other users when played on speakers.

At block 212, the processor processes the vibration signal 208 with an ASR voice transformation for improved detection of words, including keywords. For example, a user can state command phrases, such as "talk to John" to initiate a conversation with a colleague. In some examples, the safety glasses may have on-board keyword and small vocabulary command recognition for such tasks. In some examples, large vocabulary ASR and NLP can reside on the safety glasses, or be enabled through a cloud connection. In some examples, the system can respond back to the user using text-to-speech (TTS).

At block 214, the processor transmits the vibration signal 208 processed with a human-to-human voice transformation to the hearing protectors of a colleague or other users. For example, the hearing protector of the other users may play back the processed vibration signal 208 on one or more speakers. In some examples, the safety glasses and the hearing protectors may be paired before use.

At block 216, the processor may receive speech in response to the transmission as part of a conversation between a user and one or more other users. For example, when a user wants to initiate a conversation with a colleague, the user may state: "John, do I need to go left or right?" The glasses can capture the speech signal, and the keyword recognizer can recognize the identifier "John." A connection can be established between the user and the user "John" and processed speech audio transmitted to the apparatus associated with the identifier "John." These signals can then be played back through the hearing protector speakers of the device associated with the identifier "John." In some examples, the device associated with the identifier "John" may captured and process speech and return processed speech audio to the processor in response. The processor may then send the received speech to the paired hearing protector for playback.

As shown at block 222, the hearing protectors can be equipped with one or more microphones. For example, the microphones may be located on the outside of the hearing protectors to capture ambient sounds 224.

At block 226, these input ambient sounds 224 can be loudness equalized to a target volume that is sufficiently low as to not cause any risk of hearing loss. However, the target volume may be loud enough such that cues in the ambient environment may also be preserved.

At block 228, the low volume version of the ambient sounds 224 can then be played back to the user via one or more speakers 230. In some examples, the loudness compensation can be performed digitally on board. For example, the loudness compensation can be performed using a digital signal processor in a device. In some examples, the loudness level can be preset or user adjustable.

At block 232, the processor can characterize and log incoming ambient sounds 224. For example, the ambient sounds can be characterized in terms of ⅓ octave levels over time, A-weighted levels, or raw samples. In some examples, the logged ambient sounds can be used to provide means to measure noise exposure of users. In some examples, the characterized ambient sounds can be used to assess risks and can also be used to correlate ambient sounds to events.

At block 234, the processor can characterize incoming ambient sounds 224 with an audio event classifier. For example, an audio event classifier can recognize target sounds in the environment that may be of interest. In some examples, the audio event classifier may be a neural network trained to detect any number of audio events.

At block 236, the processor logs audio events and generates notifications based on the audio events. For example, the notifications may correspond to particular sounds that are detected. In some examples, when such sounds are recognized, the system can notify the user. For example, the processor can play back a notification of a safety hazard. Thus, the hearing protector may suppress outside noise in most cases, but if there are any particularly sounds that correspond dangerous situations then the user may be alerted accordingly. For example, such dangerous situations may include fire alarms, explosions, collisions, etc.

At block 238, the processor mixes different audio together for playback. For example, the different audio may include TTS responses from block 220, feedback speech from block 216, notifications from block 236, and reduced volume ambient sounds from block 226. The processor may play back the mixed audio 228 via the speakers 230. For example, the speaker 230 may be integrated into hearing protectors.

This process flow diagram is not intended to indicate that the blocks of the example process 200 are to be executed in any particular order, or that all of the blocks are to be included in every case. Further, any number of additional blocks not shown may be included within the example process 200, depending on the details of the specific implementation.

FIG. 3A is a diagram illustrating an example graph of a raw signal including speech captured from a vibration sensor. The example graph is generally referred to by the reference number 300A.

FIG. 3A shows an example raw signal waveform 302A of speech as captured in a noisy environment via a vibration sensor using a left channel. A set experiments were conducted with a prototype device to demonstrate benefits. First, accurate binaural recordings were made in various environments with a Head and Torso Simulator (HATS) system and a binaural headphone. For example, the environments included noise in data centers, an industrial Fab, a Titanium industrial facility, and construction noise. The noise levels in these environments ranged from 80 to 110 decibels, A-weighted (dBA). Two example environments were selected for prototype tests: data center noise with levels of approximately 94 dBA, and factory heavy machinery noise of approximately 92 dBA. Note that these sound levels are extremely high and require hearing protection per federal regulations.

In the lab, a prototype system was constructed with safety glasses with integrated piezo electric vibration sensing elements, hearing protectors, and a data acquisition system. In addition to the vibration sensors, data was also simultaneously collected from regular microphones and 8 channel microphone arrays in the near field and far field. The system was located in a usability lab, and a playback speaker system was used to generate the high noise scenarios outlined above. A participant was asked to state a set of utterances that appeared on a screen, and the data from the sensors was captured. The utterances included a set of wake up words, personal assistant type utterances, and large vocabulary dictation type text.

In the particular examples of FIGS. 3A-3F, the environment included data center conditions with an ambient noise of ~94 dBA and the utterance specifically used was "Hello Computer." As can be seen in FIG. 3A, although ambient sounds are present, the captured speech can be clearly detected at a time of about 2 seconds onwards. The results of an experiment using an integrated solution with the vibration sensing elements of the techniques described herein demonstrate improved communication in noisy environments. For example, a +10 dB signal-to-noise ratio (SNR) was observed using vibration sensors without any additional processing. Thus, using the techniques described herein, speech can be clearly understood even in these extreme high noise environments.

FIG. 3B is a diagram illustrating an example graph of a raw signal including speech captured from a microphone in a noisy environment. The example graph is generally referred to by the reference number 300B.

FIG. 3B shows an example waveform 302B of speech as captured in a noisy environment via a microphone in a near field using a right channel. For example, the captured audio is the same time period as the audio captured in the left channel in FIG. 3A above. By contrast to FIG. 3A, as can be seen in FIG. 3B, the captured speech 302B cannot be distinguished from the ambient sounds, making the speech more difficult to be detected and processed. For a regular microphone, the data center high noise scenario sound-to-noise ratio (SNR) was about −20 dB. Thus, it is very difficult, even for humans, to decipher any speech in the audio signal.

FIG. 3C is a diagram illustrating an example graph of a processed signal including speech captured from a vibration sensor in a noisy environment. The example graph is generally referred to by the reference number 300C.

FIG. 3C shows an A-weighted Fast Fourier transform FFT versus time of the raw audio signal of speech captured in FIG. 3A above. As can be seen in FIG. 3C, the speech 302C can be clearly distinguished from the background ambient sounds.

FIG. 3D is a diagram illustrating an example graph of a processed signal including speech captured from a microphone in a noisy environment The example graph is generally referred to by the reference number 300D.

FIG. 3D shows an A-weighted Fast Fourier transform FFT versus time of the raw audio signal of speech captured in FIG. 3B above. As can be seen in FIG. 3D, the speech 302D can be no longer clearly distinguished from the background ambient sounds. Thus, audio captured via microphones performs worse than audio captured via vibration sensors even with transformations applied.

FIG. 3E is a diagram illustrating an example graph of another processed signal including speech captured from a vibration sensor in a noisy environment. The example graph is generally referred to by the reference number 300E.

FIG. 3E shows an A-weighted level versus time of the raw signal of speech captured in FIG. 3A above. As can be seen in FIG. 3E, the speech 302E can be clearly distinguished from the background ambient sounds by the increased A-weighted level at around 2 seconds onwards.

FIG. 3F is a diagram illustrating an example graph of another processed signal including speech captured from a microphone in noisy environment. The example graph is generally referred to by the reference number 300F.

FIG. 3F shows an A-weighted level versus time of the raw signal of speech captured in FIG. 3B above. As can be seen in FIG. 3F, the speech 302F cannot be clearly distinguished from the background ambient sounds. In particular, there is no increased A-weighted level at around 2 seconds onwards. Rather, the A-weighted level remains about the same throughout the graph 300F.

Figure 4:
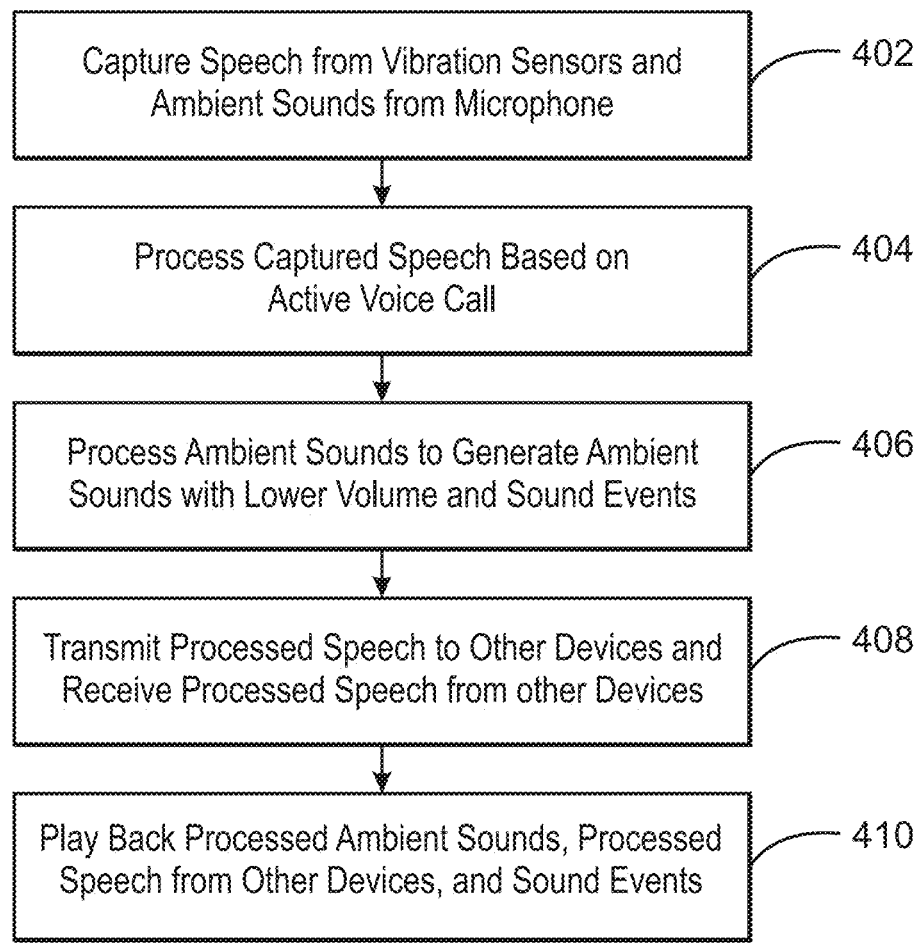
FIG. 4 is a flow chart illustrating a method for integrated hearing protection and communication.

FIG. 4 is a flow chart illustrating a method for processing and transmitting speech captured via vibration sensors. The example method is generally referred to by the reference number 400 and can be implemented in the system 100 of FIG. 1 above, the processor 702 of the computing device 700 of FIG. 7 below, or the computer readable media 800 of FIG. 8 below.

At block 402, a processor captures speech from one or more vibration sensors and ambient sounds from one or more microphones. For example, the vibration sensors may be piezoelectric sensors or accelerometers in the nose pad of an integrated hearing protection and communication apparatus.

At block 404, the processor processes the captured speech based on an active voice call. In some examples, the processor can process the speech based on a determination of whether an active voice call is detected or not detected. For example, the processor can process the speech using the method 500 described below with respect to FIG. 5.

At block 406, the processor processes ambient sounds to generate ambient sounds with a lower volume and sound events. In some examples, the processor can detect sound events from the ambient sounds and generate notifications based on the sounds events. For example, the processor can process the ambient sounds using the method 600 described below with respect to FIG. 6.

At block 408, the processor transmits processed speech to one or more other devices and receives processed speech from one or more other devices. In some examples, the processor can transmit processed speech to a device based on a detected keyword. For example, one or more devices may be associated with the detected keyword.

At block 410, the processor plays back processed ambient sounds, processed speech from other devices, and sound events. For example, the processed ambient sounds, processed speech from other devices, and sound events can be combined and played back at one or more speakers of hearing protectors in an integrated hearing protection and communication apparatus.

This process flow diagram is not intended to indicate that the blocks of the example process 400 are to be executed in any particular order, or that all of the blocks are to be included in every case. Further, any number of additional blocks not shown may be included within the example process 400, depending on the details of the specific implementation.

Figure 5:
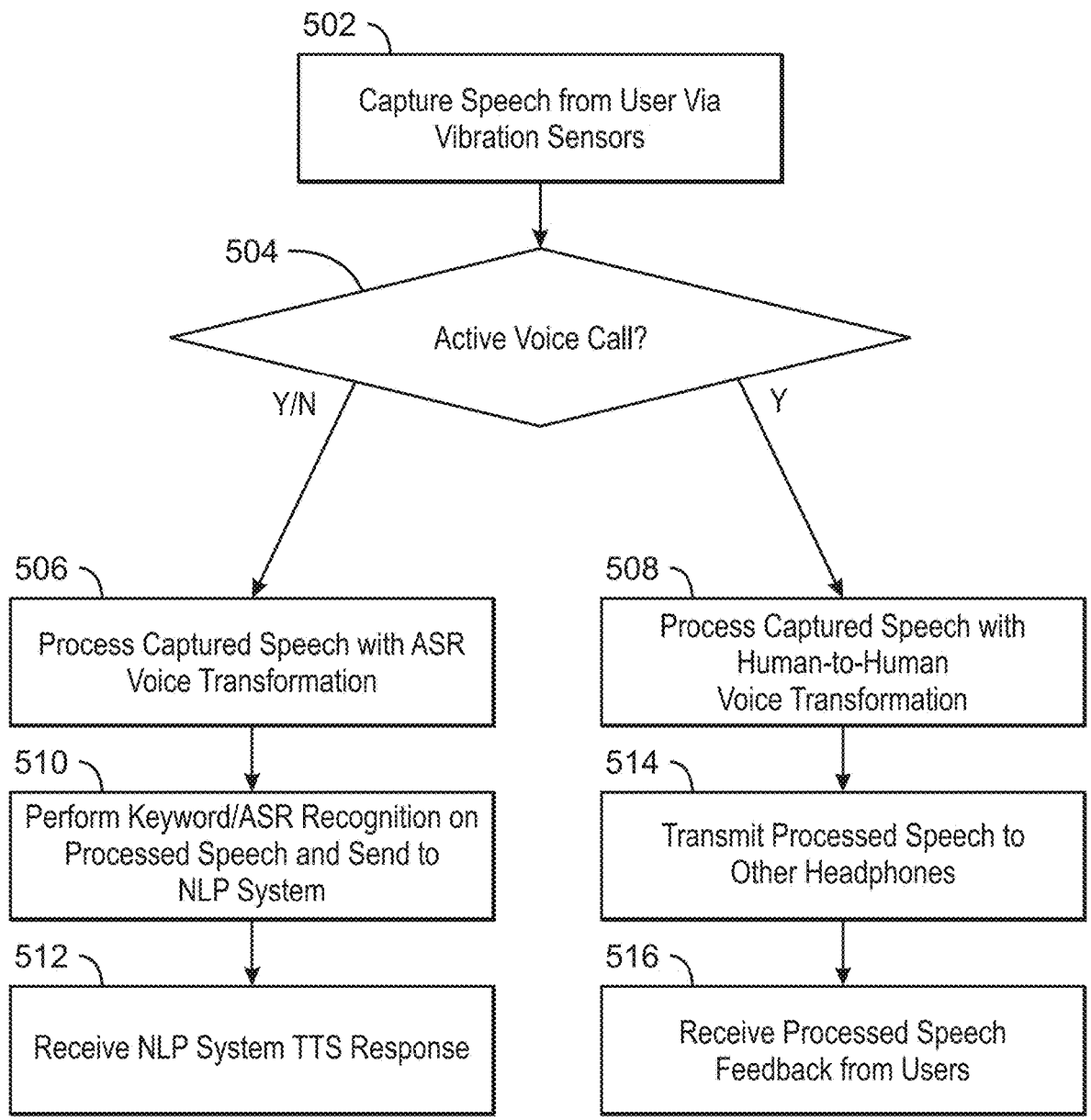
FIG. 5 is a flow chart illustrating a method for processing speech captured via vibration sensors.

FIG. 5 is a flow chart illustrating a method for processing and transmitting speech captured via vibration sensors. The example method is generally referred to by the reference number 500 and can be implemented in the system 100 of FIG. 1 above, the processor 702 of the computing device 700 of FIG. 7 below, or the computer readable media 800 of FIG. 8 below.

At block 502, a processor captures speech via one or more vibration sensors. For example, the vibration sensors may be located on the head of a speaker and can capture vibrations generated during the speech of the speaker.

At block 504, the processor determines whether a voice call is active. If the processor detects that the voice call is not active, then the method may proceed at block 506. If the processor detects that a voice call is active, then the method may proceed at blocks 506 and 508.

At block 506, the processor processes the captured speech with an automatic speech recognition (ASR) voice transformation. For example, the ASR voice transformation may be optimized for detection of keywords and phrases ASR applications.

At block 508, the processor processes the captured speech with a human-to-human voice transformation. For example, the processor may process the captured speech such that the speech is easier to understand by a human listener.

At block 510, the processor performs a keyword or ASR recognition on the processed speech and sends the recognized speech to an NLP system. For example, the NLP system can generate one or more TTS responses in response to receiving the recognized speech.

At block 512, the processor receives an NLP system TTS response. For example, the NLP system TTS response may include answers to questions, messages, notifications, etc.

At block 514, the processor causes the processed speech to be transmitted to one or more other headphones. For example, the processor can cause a transmitter to transmit the processed speech to a particular set of headphones based on a detected keyword associated with the set of headphones. In some examples, a number of devices may be associated with a particular keyword.

At block 516, the processor receives processed speech feedback from one or more users. For example, the processed speech feedback may include responses to the processed speech transmitted at block 514 above.

This process flow diagram is not intended to indicate that the blocks of the example process 500 are to be executed in any particular order, or that all of the blocks are to be included in every case. Further, any number of additional blocks not shown may be included within the example process 500, depending on the details of the specific implementation.

Figure 6:
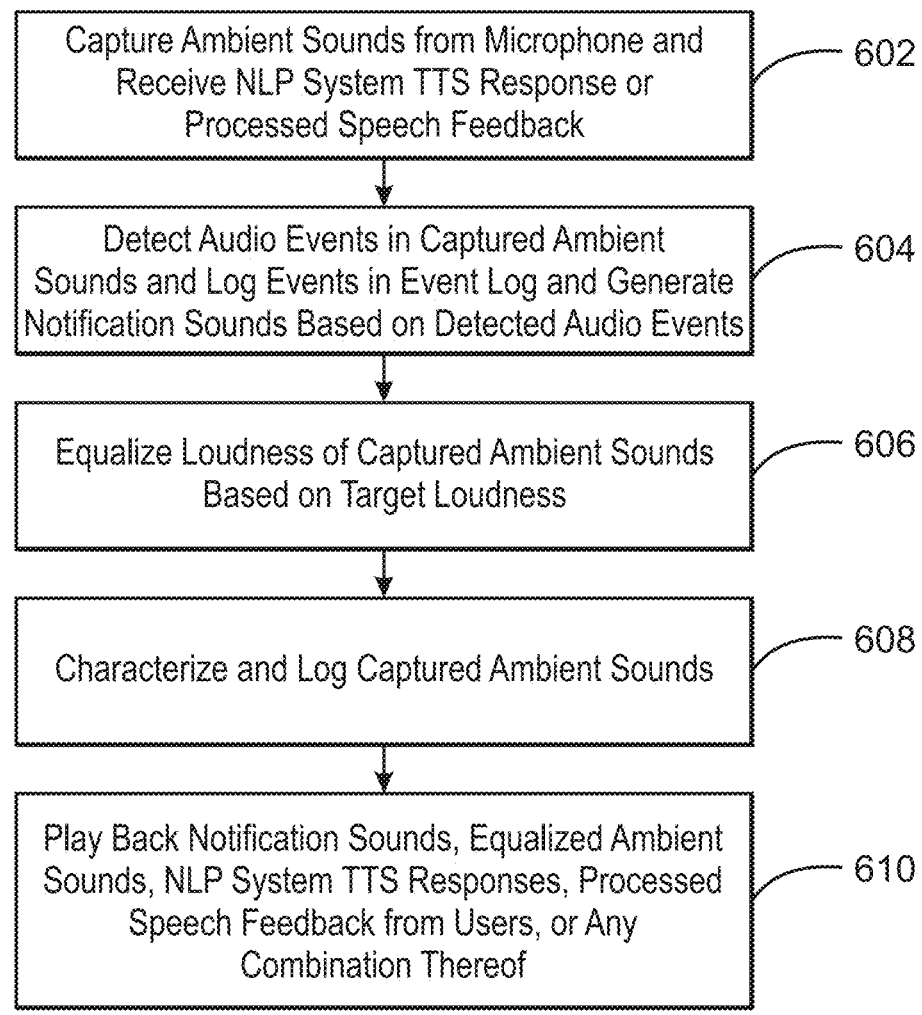
FIG. 6 is a flow chart illustrating a method for processing ambient sound.

FIG. 6 is a flow chart illustrating a method for processing ambient sound and playing back a mix of speech and ambient sound. The example method is generally referred to by the reference number 600 and can be implemented in the system 100 of FIG. 1 above, the processor 702 of the computing device 700 of FIG. 7 below, or the computer readable media 800 of FIG. 8 below.

At block 602, a processor captures ambient sounds and receives an NLP system TTS response or processed speech feedback. For example, the ambient sounds may be received from a microphone. The NLP system TTS response may be received from an NLP system. For example, the NPL system may have generated a TTS response as described above with respect to FIG. 5. In some examples, the processed speech feedback may be received from one or more external devices.

At block 604, the processor detects audio events in the captured ambient sounds and logs the audio events in an event log and generates notification sounds based on the audio events. In some examples, the notification sounds may be based on a detected type of the audio event.

At block 606, the processor equalizes a loudness of the captured ambient sounds based on a target loudness. For example, the target loudness may be an adjustable volume level that is received from a user. In some examples, the target loudness may be a present value.

At block 608, the processor characterizes and logs the captured ambient sounds. For example, the captured ambient sounds can be characterized based on one or more features of the captured ambient sounds. In some examples, the captured ambient sounds can be characterized using a pretrained neural network. For example, the neural network can be trained using a training dataset including a variety of different types of sounds. In some examples, the characterized sound can then be logged. For example, the logged characterized sound can be used later to analyze an environment such as a work environment.

At block 610, the processor plays back notification sounds, equalized ambient sounds, an NLP system TTS responses, processed speech feedback from one or more users, or any combination thereof. For example, the notification sound may correspond to one or more detected sounds in the captured ambient sound.

This process flow diagram is not intended to indicate that the blocks of the example process 600 are to be executed in any particular order, or that all of the blocks are to be included in every case. Further, any number of additional blocks not shown may be included within the example process 600, depending on the details of the specific implementation.

Figure 7:
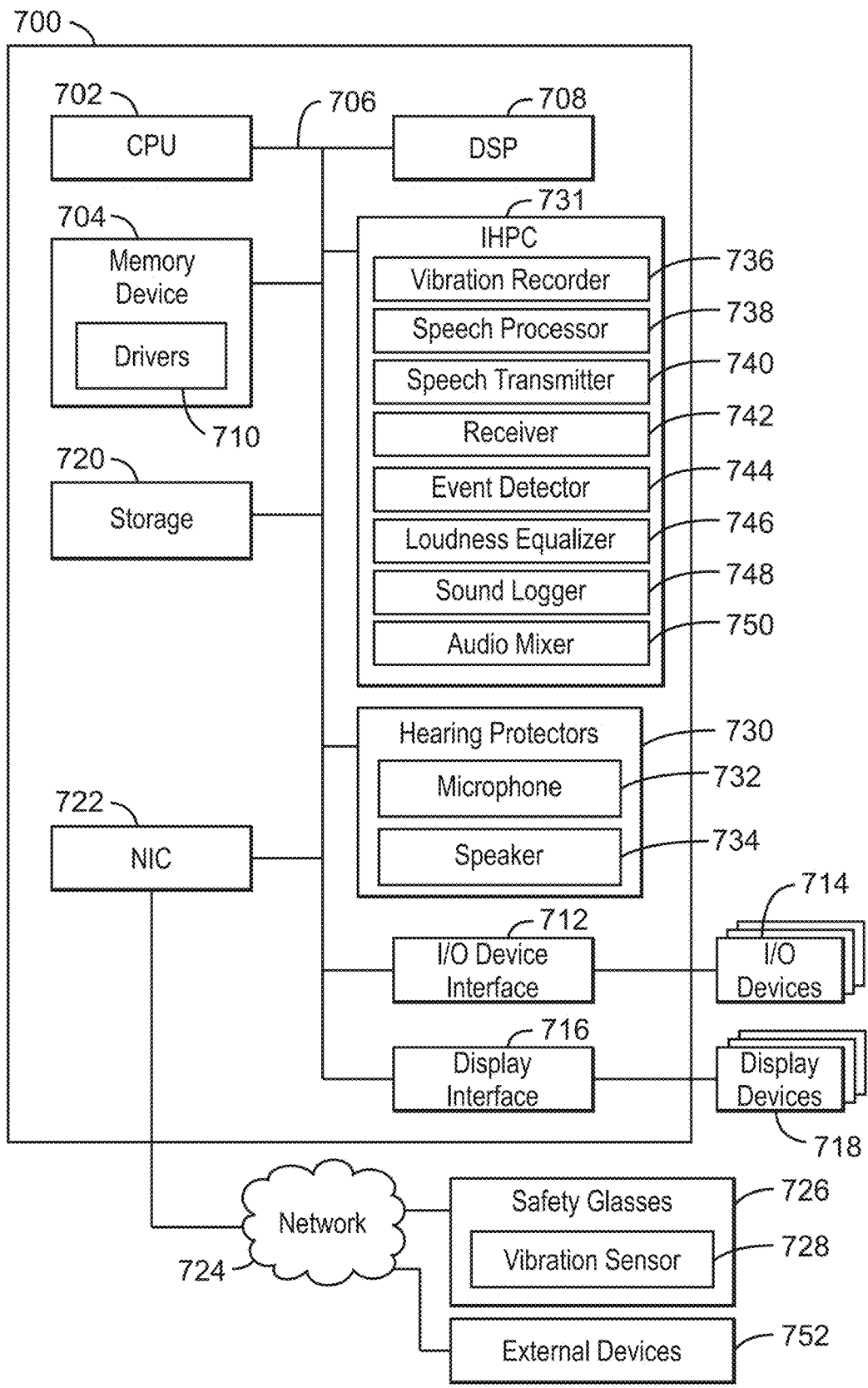
FIG. 7 is block diagram illustrating an example computing device that can communication and ear protection in noisy environments.

Referring now to FIG. 7, a block diagram is shown illustrating an example computing device that can provide communication and ear protection in noisy environments. The computing device 700 may be, for example, a laptop computer, desktop computer, tablet computer, mobile device, or wearable device, among others. In some examples, the computing device 700 may be an integrated hearing protection and communication device. The computing device 700 may include a central processing unit (CPU) 702 that is configured to execute stored instructions, as well as a memory device 704 that stores instructions that are executable by the CPU 702. The CPU 702 may be coupled to the memory device 704 by a bus 706. Additionally, the CPU 702 can be a single core processor, a multi-core processor, a computing cluster, or any number of other configurations. Furthermore, the computing device 700 may include more than one CPU 702. In some examples, the CPU 702 may be a system-on-chip (SoC) with a multi-core processor architecture. In some examples, the CPU 702 can be a specialized digital signal processor (DSP) used for image processing. The memory device 704 can include random access memory (RAM), read only memory (ROM), flash memory, or any other suitable memory systems. For example, the memory device 704 may include dynamic random access memory (DRAM).

The memory device 704 can include random access memory (RAM), read only memory (ROM), flash memory, or any other suitable memory systems. For example, the memory device 704 may include dynamic random access memory (DRAM).

The computing device 700 may also include a digital signal processing unit (DSP) 708. As shown, the CPU 702 may be coupled through the bus 706 to the DSP 708. The DSP 708 may be configured to perform any number of audio processing operations within the computing device 700. For example, the DSP 708 may be configured to measure, filter or compress continuous real-world analog signals corresponding to audio, or the like, to be played back to a user of the computing device 700.

The memory device 704 can include random access memory (RAM), read only memory (ROM), flash memory, or any other suitable memory systems. For example, the memory device 704 may include dynamic random access memory (DRAM). The memory device 704 may include device drivers 710 that are configured to execute the instructions for processing signals from vibration sensors and microphones generating audio for playback. The device drivers 710 may be software, an application program, application code, or the like.

The CPU 702 may also be connected through the bus 706 to an input/output (I/O) device interface 712 configured to connect the computing device 700 to one or more I/O devices 714. The I/O devices 714 may include, for example, a keyboard and a pointing device, wherein the pointing device may include a touchpad or a touchscreen, among others. The I/O devices 714 may be built-in components of the computing device 700, or may be devices that are externally connected to the computing device 700. In some examples, the memory 704 may be communicatively coupled to I/O devices 714 through direct memory access (DMA).

The CPU 702 may also be linked through the bus 706 to a display interface 716 configured to connect the computing device 700 to a display device 718. The display device 718 may include a display screen that is a built-in component of the computing device 700. The display device 718 may also include a computer monitor, television, or projector, among others, that is internal to or externally connected to the computing device 700.

The computing device 700 also includes a storage device 720. The storage device 720 is a physical memory such as a hard drive, an optical drive, a thumbdrive, an array of drives, a solid-state drive, or any combinations thereof. The storage device 720 may also include remote storage drives.

The computing device 700 may also include a network interface controller (NIC) 722. The NIC 722 may be configured to connect the computing device 700 through the bus 706 to a network 724. The network 724 may be a wide area network (WAN), local area network (LAN), or the Internet, among others. In some examples, the device may communicate with other devices through a wireless technology. For example, the device may communicate with other devices via a wireless local area network connection. In some examples, the device may connect and communicate with other devices via Bluetooth® or similar technology.

The computing device 700 further includes a set of safety glasses 726 with vibration sensor 728. For example, the safety glasses 726 may have extended panels to prevent objects from going behind the glasses. In some examples, the safety glasses 726 may be made of a hi-transparency polycarbonate hardened for high impact. In some examples, the vibration sensor 728 may be a piezoelectric sensor or an accelerometer, among other sensors that can detect vibrations. In some examples, the vibration sensor 728 may be located on the nose pad of the safety glasses 726. The vibration sensor 728 can capture vibrations at a nose that are associated with speech. For example, the vibrations at the nose may be caused by a user speaking.

The computing device 700 further includes a hearing protectors 730. The hearing protectors 730 may include a microphone 732 and a speaker 734. For example, the microphone 732 may be used to capture ambient sound from the environment of the hearing protectors 730. The speaker 734 may be used to play back audio. In some examples, the audio may include ambient sounds with reduced volume, notifications, speech from other devices, or TTS responses, among other types of audio.

The computing device 700 further includes an integrated hearing protector and communicator (IHPC) 731. For example, the IHPC 731 can be used to protecting hearing and enable communication in environments with loud noise. For example, an environment with loud noise may include noise with an amplitude of 85 dBA or more. The IHPC 731 can include a vibration recorder 736, a speech processor 738, a speech transmitter 740, a receiver 742, an event detector 744, a loudness equalizer 746, a sound logger 748, and an audio mixer 750. In some examples, each of the components 736-750 of the IHPC 731 may be a microcontroller, embedded processor, or software module. The vibration recorder 736 can capture speech from a user. The speech processor 738 can process the speech based on an active voice call. For example, the speech processor 738 can process the captured speech with an automatic speech recognition (ASR) voice transformation in response to not detecting an active voice call. In some examples, the speech processor 738 can process the captured speech with a human-to-human voice transformation and an ASR transformation in response to detecting an active voice call. For example, a destination of the active voice call may be an external IHPC or other device that can play back audio for human consumption. The speech transmitter 740 can transmit the captured speech to one or more other devices. In some examples, the speech transmitter 740 can transmit the captured speech to one or more other devices based on a detected destination of the speech. For example, the speech transmitter 740 can send the speech to one or more devices based on a detected keyword associated with the one or more devices. The receiver 742 can receive processed speech feedback received from other devices. The event detector 744 can detect an audio event in the ambient sound and log the audio event. For example, the audio event may correspond to alarms, sudden loud noises or glass breaking. In some examples, the event detector 744 can generate a notification based on the detected audio event. The loudness equalizer 746 can reduce a volume of an ambient sound. For example, the loudness equalizer 746 can equalize the loudness of the captured ambient sounds based on a target loudness. The sound logger 748 can log ambient sounds. For example, the logged ambient sounds can be used to can be used to provide means to measure noise exposure of users. The audio mixer 750 can combine the processed ambient sounds, processed speech feedback received from other devices, and the notifications. For example, the combined processed ambient sounds, processed speech feedback received from other devices, and notifications can then be played back on a device, such as the speakers 734 of the hearing protectors 730.

The computing device 700 can further be communicatively coupled to one or more external devices 752. In some examples, the computing device 700 can send and receive processed audio to the external device 752. For example, the external devices 752 may be integrated hearing protection and communication devices.

The block diagram of FIG. 7 is not intended to indicate that the computing device 700 is to include all of the components shown in FIG. 7. Rather, the computing device 700 can include fewer or additional components not illustrated in FIG. 7, such as additional buffers, additional processors, and the like. The computing device 700 may include any number of additional components not shown in FIG. 7, depending on the details of the specific implementation. Furthermore, any of the functionalities of the vibration recorder 736, the speech processor 738, the speech transmitter 740, the receiver 742, the event detector 744, the loudness equalizer 746, the sound logger 748, and the sound mixer 750, may be partially, or entirely, implemented in hardware and/or in the processor 702. For example, the functionality may be implemented with an application specific integrated circuit, in logic implemented in the processor 702, or in any other device. In addition, any of the functionalities of the CPU 702 may be partially, or entirely, implemented in hardware and/or in a processor. For example, the functionality of the IHPC 731 may be implemented with an application specific integrated circuit, in logic implemented in a processor, in logic implemented in a specialized audio processing unit such as the DSP 708, or in any other device.

Figure 8:
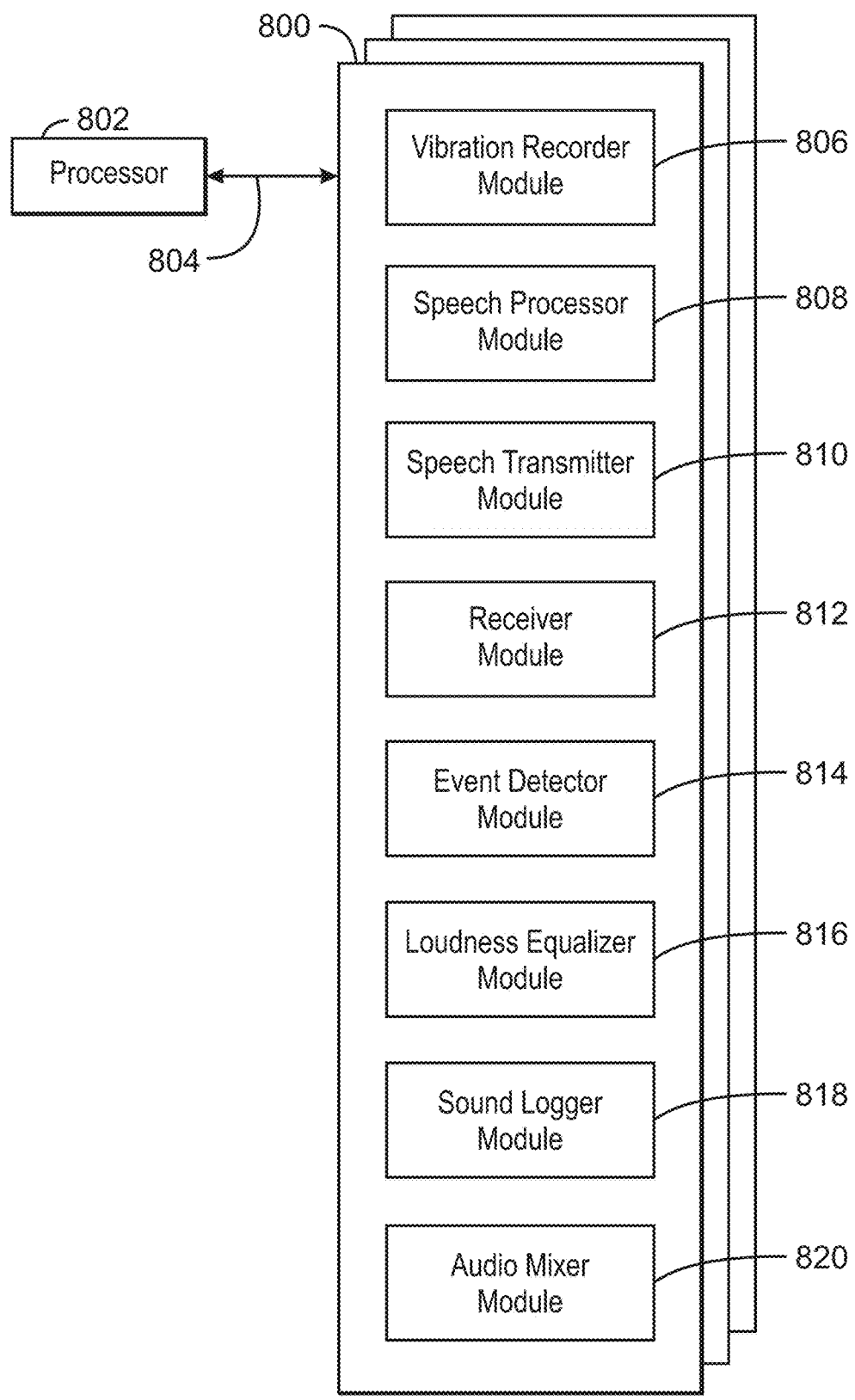
FIG. 8 is a block diagram showing computer readable media that store code for providing communication and ear protection in noisy environments.

FIG. 8 is a block diagram showing computer readable media 800 that store code for providing communication and ear protection in noisy environments. The computer readable media 800 may be accessed by a processor 802 over a computer bus 804. Furthermore, the computer readable medium 800 may include code configured to direct the processor 802 to perform the methods described herein. In some embodiments, the computer readable media 800 may be non-transitory computer readable media. In some examples, the computer readable media 800 may be storage media.

The various software components discussed herein may be stored on one or more computer readable media 800, as indicated in FIG. 8. For example, a vibration recorder module 806 may be configured to capture speech from a vibration sensor of a first device. For example, the first device may be an integrated hearing protection and communication device. A speech processor module 808 may be configured to process the captured speech based on an active voice call. In some examples, the speech processor module 808 may be configured to process the captured speech with an automatic speech recognition (ASR) voice transformation and a human-to-human voice transformation in response to detecting an active voice call. In some examples, the speech processor module 808 may be configured to process the captured speech with an automatic speech recognition (ASR) voice transformation in response to not detecting an active voice call. In some examples, the speech processor module 808 may be configured to perform a keyword or ASR recognition on the processed speech and sending the recognition results to a natural language processing (NLP) system. A speech transmitter module 810 may be configured to transmit the captured speech to one or more other devices. For example, the speech transmitter module 810 may be configured to send the captured speech to a device based on a detected keyword. A receiver module 812 may be configured to receive ambient sounds from a microphone of a first device. In some examples, the receiver module 812 may be configured to receive a text-to-speech (TTS) response from an NLP system. An event detector module 814 may be configured to detect audio events in the captured audio sounds and log the events in an event log. In some examples, the event detector module 814 may be configured to generate notification sounds based on the detected audio events. For example, the notification sounds may be hazard notifications, among other types of notifications. A loudness equalizer module 816 may be configured to process the ambient sounds to generate ambient sounds with lower volume. For example, the loudness equalizer module 816 may be configured to equalize the loudness of the captured ambient sounds based on a target loudness. For example, the target loudness may be present and user adjustable. A sound logger module 818 may be configured to characterize and log the ambient sounds. For example, the sound logger module 818 may include a neural network trained to characterize the ambient sounds. An audio mixer module 820 may be configured to combine processed ambient sounds, processed speech feedback received from other devices, and the notifications, for playback. The combined processed ambient sounds, processed speech feedback received from other devices, and the notifications can then be played back on speakers of an integrated hearing protection and communication device.

The block diagram of FIG. 8 is not intended to indicate that the computer readable media 800 is to include all of the components shown in FIG. 8. Further, the computer readable media 800 may include any number of additional components not shown in FIG. 8, depending on the details of the specific implementation.

EXAMPLES

Example 1 is an apparatus for hearing protection and communication. The apparatus includes safety glasses including a vibration sensor to capture speech from a user. The apparatus includes hearing protectors communicatively coupled to the safety glasses and one or more other devices. The hearing protectors are to reduce a volume of an ambient sound and play back captured speech from the one or more other devices. The apparatus includes a plurality of wireless communication elements to communicatively couple the safety glasses, the hearing protectors, and a second apparatus for hearing protection and communication.

Example 2 includes the apparatus of example 1, including or excluding optional features. In this example, the wireless communication elements include short-range devices.

Example 3 includes the apparatus of any one of examples 1 to 2, including or excluding optional features. In this example, vibration sensor includes a piezoelectric sensor or an accelerometer.

Example 4 includes the apparatus of any one of examples 1 to 3, including or excluding optional features. In this example, the vibration sensor is integrated into a nose pad of the safety glasses.

Example 5 includes the apparatus of any one of examples 1 to 4, including or excluding optional features. In this example, the hearing protectors include a microphone to capture the ambient sound.

Example 6 includes the apparatus of any one of examples 1 to 5, including or excluding optional features. In this example, the hearing protectors include a speaker to playback audio including the ambient sound with reduced volume and the captured speech.

Example 7 includes the apparatus of any one of examples 1 to 6, including or excluding optional features. In this example, the hearing protectors are to further generate a notification based on the ambient sound.

Example 8 includes the apparatus of any one of examples 1 to 7, including or excluding optional features. In this example, the hearing protectors are to detect an audio event in the ambient sound and log the audio event.

Example 9 includes the apparatus of any one of examples 1 to 8, including or excluding optional features. In this example, the hearing protectors include a voice transformer to process the speech based on a detected active voice call.

Example 10 includes the apparatus of any one of examples 1 to 9, including or excluding optional features. In this example, the hearing protectors are to detect a target device to send the captured speech based a detected destination of the speech, the target device including the second apparatus for hearing protection and communication.

Example 11 is a method for hearing protection and communication. The method includes capturing speech from a vibration sensor and ambient sounds from a microphone of a first device. The method also includes processing, via the processor, the captured speech based on an active voice call. The method further includes processing the ambient sounds to generate ambient sounds with lower volume and notifications based on detected sound events. The method also further includes playing back the processed ambient sounds, processed speech feedback received from other devices, and the notifications.

Example 12 includes the method of example 11, including or excluding optional features. In this example, the method includes transmitting the processed speech to the other devices and receiving the processed speech feedback from one or more of the other devices.

Example 13 includes the method of any one of examples 11 to 12, including or excluding optional features. In this example, processing the captured speech includes processing the captured speech with an automatic speech recognition (ASR) voice transformation and a human-to-human voice transformation in response to detecting the active voice call.

Example 14 includes the method of any one of examples 11 to 13, including or excluding optional features. In this example, processing the captured speech includes processing the captured speech with an automatic speech recognition (ASR) voice transformation in response to not detecting the active voice call.

Example 15 includes the method of any one of examples 11 to 14, including or excluding optional features. In this example, the method includes performing a keyword or ASR recognition on the processed speech and sending the recognition results to a natural language processing (NLP) system.

Example 16 includes the method of any one of examples 11 to 15, including or excluding optional features. In this example, the method includes receiving a text-to-speech (TTS) response from the NLP system and playing back the TTS response.

Example 17 includes the method of any one of examples 11 to 16, including or excluding optional features. In this example, the method includes sending the captured speech to a device based on a detected keyword.

Example 18 includes the method of any one of examples 11 to 17, including or excluding optional features. In this example, the method includes detecting audio events in the captured audio sounds and logging the events in an event log and generating notification sounds based on the detected audio events.

Example 19 includes the method of any one of examples 11 to 18, including or excluding optional features. In this example, the method includes equalizing the loudness of the captured ambient sounds based on a target loudness.

Example 20 includes the method of any one of examples 11 to 19, including or excluding optional features. In this example, the method includes characterizing and logging the ambient sounds.

Example 21 is at least one computer readable medium for hearing protection and communication having instructions stored therein that direct the processor to capture speech from a vibration sensor and ambient sounds from a microphone of a first device. The computer-readable medium also includes instructions that direct the processor to process the captured speech based on an active voice call. The computer-readable medium further includes instructions that direct the processor to transmit the captured speech to one or more other devices. The computer-readable medium also further includes instructions that direct the processor to play back the processed ambient sounds, processed speech feedback received from other devices, and the sound events.

Example 22 includes the computer-readable medium of example 21, including or excluding optional features. In this example, the computer-readable medium includes instructions to process the ambient sounds to generate ambient sounds with lower volume and sound events.

Example 23 includes the computer-readable medium of any one of examples 21 to 22, including or excluding optional features. In this example, the computer-readable medium includes instructions to process the captured speech with an automatic speech recognition (ASR) voice transformation and a human-to-human voice transformation in response to detecting the active voice call.

Example 24 includes the computer-readable medium of any one of examples 21 to 23, including or excluding optional features. In this example, the computer-readable medium includes instructions to process the captured speech with an automatic speech recognition (ASR) voice transformation in response to not detecting the active voice call.

Example 25 includes the computer-readable medium of any one of examples 21 to 24, including or excluding optional features. In this example, the computer-readable medium includes instructions to perform a keyword or ASR recognition on the processed speech and sending the recognition results to a natural language processing (NLP) system.

Example 26 includes the computer-readable medium of any one of examples 21 to 25, including or excluding optional features. In this example, the computer-readable medium includes instructions to receive a text-to-speech (TTS) response from the NLP system and playing back the TTS response.

Example 27 includes the computer-readable medium of any one of examples 21 to 26, including or excluding optional features. In this example, the computer-readable medium includes instructions to send the captured speech to a device based on a detected keyword.

Example 28 includes the computer-readable medium of any one of examples 21 to 27, including or excluding optional features. In this example, the computer-readable medium includes instructions to detect audio events in the captured audio sounds and log the events in an event log and generating notification sounds based on the detected audio events.

Example 29 includes the computer-readable medium of any one of examples 21 to 28, including or excluding optional features. In this example, the computer-readable medium includes instructions to equalize the loudness of the captured ambient sounds based on a target loudness.

Example 30 includes the computer-readable medium of any one of examples 21 to 29, including or excluding optional features. In this example, the computer-readable medium includes instructions to characterize and log the ambient sounds.

Example 31 is a system for hearing protection and communication. The system includes safety glasses including a vibration sensor to capture speech from a user. The system includes hearing protectors communicatively coupled to the safety glasses and one or more other devices. The hearing protectors are to reduce a volume of an ambient sound and play back captured speech from the one or more other devices. The system includes a plurality of wireless communication elements to communicatively couple the safety glasses, the hearing protectors, and a second set of safety glasses and hearing protectors for hearing protection and communication.

Example 32 includes the system of example 31, including or excluding optional features. In this example, the wireless communication elements include short-range devices.

Example 33 includes the system of any one of examples 31 to 32, including or excluding optional features. In this example, vibration sensor includes a piezoelectric sensor or an accelerometer.

Example 34 includes the system of any one of examples 31 to 33, including or excluding optional features. In this example, the vibration sensor is integrated into a nose pad of the safety glasses.

Example 35 includes the system of any one of examples 31 to 34, including or excluding optional features. In this example, the hearing protectors include a microphone to capture the ambient sound.

Example 36 includes the system of any one of examples 31 to 35, including or excluding optional features. In this example, the hearing protectors include a speaker to playback audio including the ambient sound with reduced volume and the captured speech.

Example 37 includes the system of any one of examples 31 to 36, including or excluding optional features. In this example, the hearing protectors are to further generate a notification based on the ambient sound.

Example 38 includes the system of any one of examples 31 to 37, including or excluding optional features. In this example, the hearing protectors are to detect an audio event in the ambient sound and log the audio event.

Example 39 includes the system of any one of examples 31 to 38, including or excluding optional features. In this example, the hearing protectors include a voice transformer to process the speech based on a detected active voice call.

Example 40 includes the system of any one of examples 31 to 39, including or excluding optional features. In this example, the hearing protectors are to detect a target device to send the captured speech based a detected destination of the speech, the target device including the second set of safety glasses and hearing protectors for hearing protection and communication.

Example 41 is a system for hearing protection and communication. The system includes means for capturing speech from a user. The system also includes means for reducing a volume of an ambient sound and playing back captured speech from the one or more other devices communicatively coupled to the means for capturing speech from a user and one or more other devices. The system further includes means for communicatively coupling the means for capturing speech from the user, the means for reducing the volume of the ambient sound and playing back captured speech, and a second set of means for capturing speech from the user and means for reducing the volume of the ambient sound and playing back captured speech.

Example 42 includes the system of example 41, including or excluding optional features. In this example, the means for communicatively coupling include short-range devices.

Example 43 includes the system of any one of examples 41 to 42, including or excluding optional features. In this example, means for capturing speech includes a piezoelectric sensor or an accelerometer.

Example 44 includes the system of any one of examples 41 to 43, including or excluding optional features. In this example, the means for capturing speech is integrated into a nose pad of the safety glasses.

Example 45 includes the system of any one of examples 41 to 44, including or excluding optional features. In this example, the means for reducing the volume of the ambient sound and playing back the captured speech include a microphone to capture the ambient sound.

Example 46 includes the system of any one of examples 41 to 45, including or excluding optional features. In this example, the means for reducing the volume of the ambient sound and playing back the captured speech include a speaker to playback audio including the ambient sound with reduced volume and the captured speech.

Example 47 includes the system of any one of examples 41 to 46, including or excluding optional features. In this example, the means for reducing the volume of the ambient sound and playing back the captured speech are to further generate a notification based on the ambient sound.

Example 48 includes the system of any one of examples 41 to 47, including or excluding optional features. In this example, the means for reducing the volume of the ambient sound and playing back the captured speech are to detect an audio event in the ambient sound and log the audio event.

Example 49 includes the system of any one of examples 41 to 48, including or excluding optional features. In this example, the means for reducing the volume of the ambient sound and playing back the captured speech include a voice transformer to process the speech based on a detected active voice call.

Example 50 includes the system of any one of examples 41 to 49, including or excluding optional features. In this example, the means for reducing the volume of the ambient sound and playing back the captured speech are to detect a target device to send the captured speech based a detected destination of the speech, the target device including the second set of means for capturing speech from the user and means for reducing the volume of the ambient sound and playing back captured speech.

Not all components, features, structures, characteristics, etc. described and illustrated herein need be included in a particular aspect or aspects. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some aspects have been described in reference to particular implementations, other implementations are possible according to some aspects. Additionally, the arrangement and/or order of circuit elements or other features illustrated in the drawings and/or described herein need not be arranged in the particular way illustrated and described. Many other arrangements are possible according to some aspects.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

It is to be understood that specifics in the aforementioned examples may be used anywhere in one or more aspects. For instance, all optional features of the computing device described above may also be implemented with respect to either of the methods or the computer-readable medium described herein. Furthermore, although flow diagrams and/or state diagrams may have been used herein to describe aspects, the techniques are not limited to those diagrams or to corresponding descriptions herein. For example, flow need not move through each illustrated box or state or in exactly the same order as illustrated and described herein.

The present techniques are not restricted to the particular details listed herein. Indeed, those skilled in the art having the benefit of this disclosure will appreciate that many other variations from the foregoing description and drawings may be made within the scope of the present techniques. Accordingly, it is the following claims including any amendments thereto that define the scope of the present techniques.

What is claimed is:

1. A wearable electronic device comprising:
   means for transducing vibrations associated with speech into a first signal;
   means for transducing sound associated with ambient noise into a second signal; and
   means for processing to:
      cause a speaker to output a third signal to reduce the ambient noise;
      detect an identifier in the speech;
      identify one of a second device or a third device as associated with the identifier; and
      cause a fourth signal representative of the speech to be transmitted to the identified one of the second device or the third device associated with the identifier, the second device different than the wearable electronic device, the third device different than the second device and different than the wearable electronic device.

2. The wearable electronic device of claim 1, further including means for filtering the first signal.

3. The wearable electronic device of claim 1, further including glasses, the vibrating transducing means carried by the glasses.

4. The wearable electronic device of claim 1, further including headphones, the sound transducing means carried by the headphones.

5. The wearable electronic device of claim 1, further including means for reducing a volume of the ambient noise in response to instructions from the processing means.

6. The wearable electronic device of claim 1, wherein the processing means is to cause establishment of a communication link with the second device or the third device based on the identifier.

7. The wearable electronic device of claim 6, the processing means is to cause the speaker to output speech received from one or more of the second device or the third device.

8. The wearable electronic device of claim 1, wherein the identifier is associated with a user of the second device or the third device.

9. The wearable electronic device of claim 1, wherein the processing means is to:
   identify a sound event in the ambient noise, the sound event different than the speech; and
   cause the speaker to output one of the sound event or an alert indicative of the sound event in response to the identification of the sound event.

10. A first device comprising:
   memory;
   machine-readable instructions; and
   processor circuitry to execute the machine-readable instructions to:

identify a first keyword in speech associated with signals output by a vibration sensor;

cause first signals corresponding to the speech to be transmitted to one of a second device or a third device based on the first keyword, the second device different than the first device, the third device different than the first device and different than the second device; and cause a speaker to output sound corresponding to second signals, the second signals different than the first signals, the second signals corresponding to one or more of (a) speech received from the second device or (b) speech received from the third device, the speech received from the one or more of the second device or the third device including a second keyword, the second keyword associated with the first device.

11. The first device of claim 10, wherein the processor circuitry is to:

execute a neural network model to identify a sound event in the ambient noise, the sound event different than the speech associated with the signals output by the vibration sensor, different than the speech from the second device, and different than the speech from the third device; and cause the speaker to output the sound event.

12. The first device of claim 10, wherein the processor circuitry is to:

detect a sound event in the ambient noise, the sound event different than the speech associated with the signals output by the vibration sensor, different than the speech from the second device, and different than the speech from the third device; and cause the speaker to output (1) another sound to cancel ambient noise, and (2) the sound event.

13. The first device of claim 10, wherein the first keyword includes an identifier associated with a user of the second device and the processor circuitry is to cause the first signals to be transmitted to the second device.

14. A non-transitory computer readable storage medium comprising instructions that cause processor circuitry of a first device to at least:

identify a sound event in ambient noise, the ambient noise represented by signals output by a microphone;

cause a speaker to output an alert in response to the identification of the sound event;

identify a keyword in speech, the speech represented by signals output by a vibration sensor, the speech different than the sound event;

select one of a second device or a third device to receive the speech based on the keyword; and cause first audio data corresponding to the speech to be transmitted to the selected one of the second device or the third device, the second device different than the first device, the third device different than the first device and different than the second device.

15. The non-transitory computer readable storage medium of claim 14, wherein the processor circuitry is to cause the speaker to output a signal to reduce the ambient noise.

16. The non-transitory computer readable storage medium of claim 14, wherein the processor circuitry is to cause the speaker to output sound to cancel the ambient noise.

17. The non-transitory computer readable storage medium of claim 14, wherein the processor circuitry is to cause establishment of a communication link with the second device or the third device in response to the selection.

18. The non-transitory computer readable storage medium of claim 14, wherein the sound event is a first sound event, the ambient noise is first ambient noise, and the processor circuitry is to detect a second sound event in second ambient noise based on the first sound event, the second ambient noise represented by signals output by the microphone after the signals associated with the first ambient noise.

19. The non-transitory computer readable storage medium of claim 14, wherein the processor circuitry is to cause the speaker to output speech from one of the second device or the third device.

20. The non-transitory computer readable storage medium of claim 14, wherein the keyword includes an identifier associated with a user of the second device or the third device.

* * * * *